United States Patent [19]
Taylor

[11] 3,952,742
[45] Apr. 27, 1976

[54] NEEDLE-CARRIED, TRANSTHORACIC, CANNULA-TYPE CARDIAC RESUSCITATION INSTRUMENT

[76] Inventor: Duane F. Taylor, 680 Winter St., SE., Salem, Oreg. 97301

[22] Filed: June 12, 1974

[21] Appl. No.: 478,790

[52] U.S. Cl............................ 128/172.1; 128/347; 128/348; 128/418; 128/419 P
[51] Int. Cl.²................... A61M 25/00; A61N 1/04
[58] Field of Search............. 128/172.1, 419 P, 418, 128/404, 349 B, 349 BV, 350 R, 2.06 E, 348, 349, 2.06 E, DIG. 4, 347

[56] References Cited
UNITED STATES PATENTS

| | | | |
|---|---|---|---|
| 3,411,506 | 11/1968 | Velasco | 128/350 R |
| 3,459,175 | 8/1969 | Miller | 128/349 BY |
| 3,516,412 | 6/1970 | Ackerman | 128/419 P |
| 3,533,403 | 10/1970 | Woodson | 128/172.1 |
| 3,680,544 | 8/1972 | Shinnick | 128/172.1 |
| 3,717,151 | 2/1973 | Collett | 128/350 R |
| 3,788,328 | 1/1974 | Alley | 128/350 R |

Primary Examiner—Robert W. Michell
Assistant Examiner—Lee S. Cohen
Attorney, Agent, or Firm—Kolisch, Hartwell, Dickinson & Stuart

[57] ABSTRACT

A transthoracic, cannula-type cardiac resuscitation instrument for use in conjunction with a rigid catheter-like needle, and adapted for rapid penetration of and placement in the wall of a person's heart. The instrument includes an elongated flexible tube which permits free axial insertion and withdrawal of such a needle for the purpose of the needle acting, among other things, as a rigid penetration and carrying device for carrying the tube into proper position with respect to a heart. The proposed tube, adjacent its distal end (which penetrates a heart wall during use) carries a pair of axially spaced inflatable-deflatable balloons that are positioned on opposite sides of an exposed electrical conductor usable for supplying electrical pacing pulses to a heart. After placement of the tube, and withdrawal of a needle, the tube may be used for injection of medications into the heart.

13 Claims, 4 Drawing Figures

U.S. Patent April 27, 1976 3,952,742
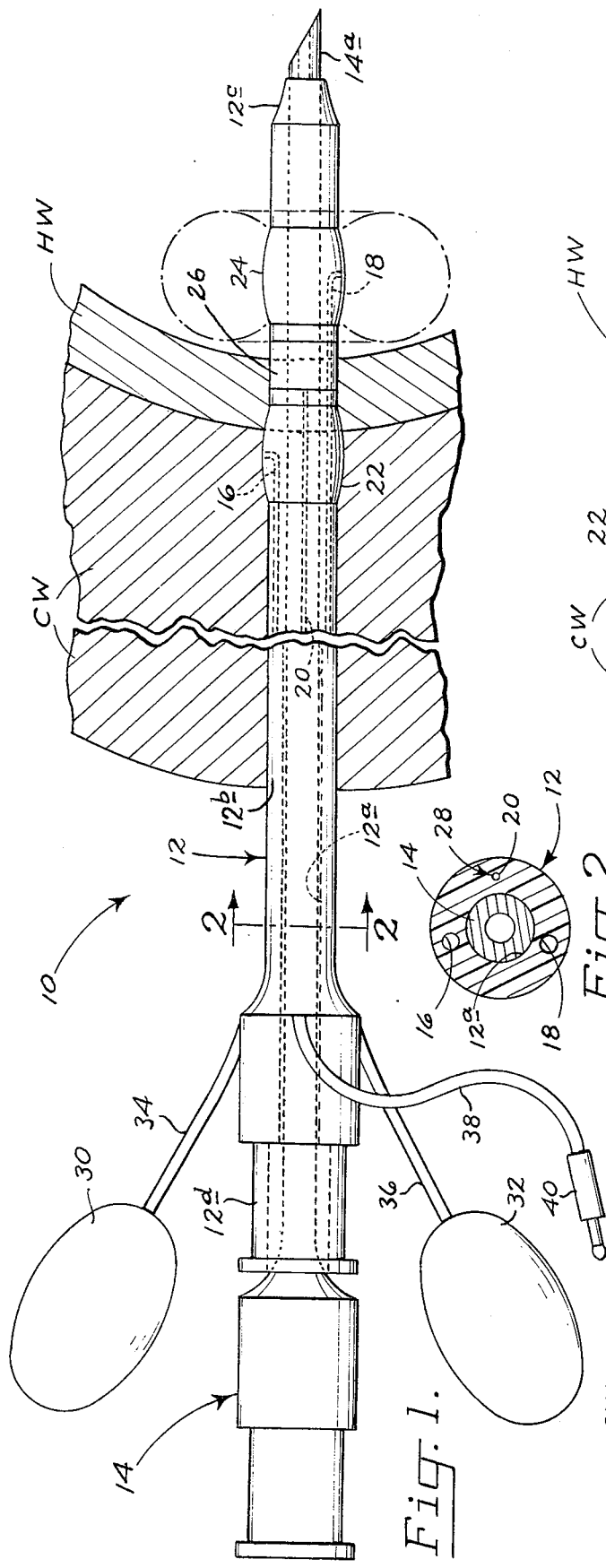
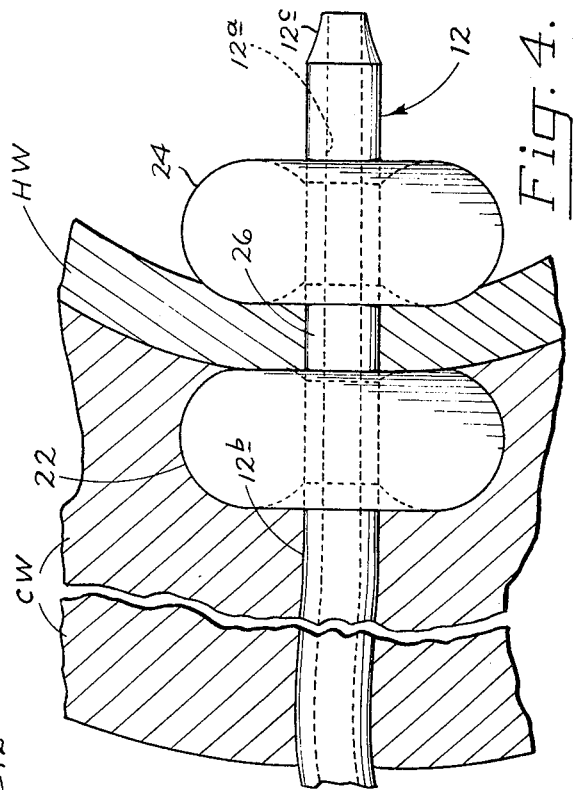
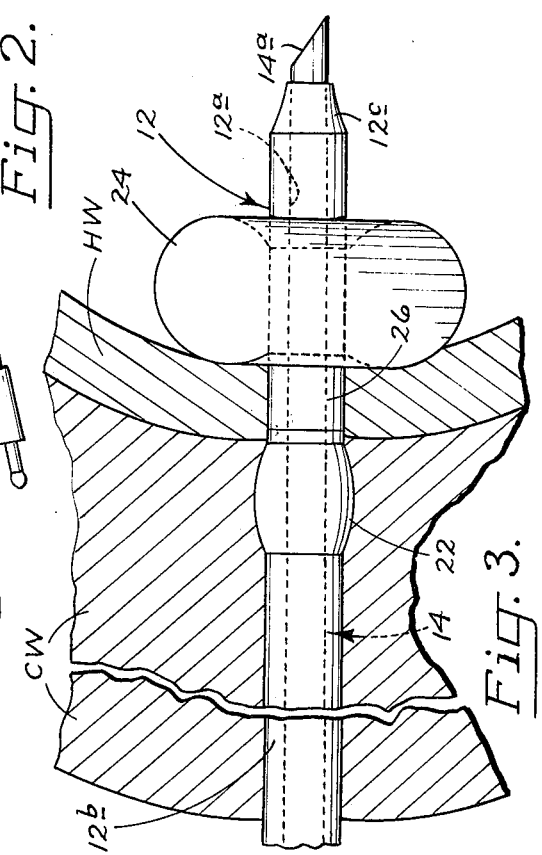

NEEDLE-CARRIED, TRANSTHORACIC, CANNULA-TYPE CARDIAC RESUSCITATION INSTRUMENT

BACKGROUND AND SUMMARY OF THE INVENTION

This invention pertains to a cardiac resuscitation instrument, and more particularly, to a cannula-type resuscitation instrument adapted for transthoracic insertion into and through the wall of a person's heart.

As is well known, cardiac resuscitation is an operation which must be performed extremely quickly, not only to save a person's life, but also to prevent irreversible brain and heart damage. Conventional resuscitation steps take several forms, including so-called external heart massage, injection of medications into the heart, and electrical pacing of the heart.

A general object of the present invention is to provide a novel transthoracic, cannula-type cardiac resuscitation instrument which facilitates rapid, "one-shot" insertion and placement in the wall of a heart, and which thereafter facilitates both immediate injection of medications directly into the heart, as well as electrical pacing of the heart.

Featured in the invention, according to a preferred embodiment thereof, is an elongated flexible tube whose central passage permits free axial insertion and withdrawal of a catheter-like needle—this tube being somewhat shorter than the needle with which it is intended to be used. Mounted on the tube adjacent its distal end are two axially spaced inflatable-deflatable balloons which are positioned on opposite sides of an exposed electrically conductive expanse. Passages are provided in the wall of the tube for enabling selective and independent inflation and deflation of the balloons, and also for carrying a conductor which is connected to the just-mentioned conductive expanse.

During use of this apparatus, the catheter needle, or the like, is inserted into the tube, with the distal end of the needle exposed and extending beyond the distal end of the tube. The needle tip acts as a means for puncturing a person's chest and heart walls, with the body of the prong in the needle acting as a rigid carrier for the tube during its insertion.

As will be explained more fully below, following penetration of a heart wall, the balloons are inflated, one after another, to lock the tube against axial retraction from the heart wall, and also to position the conductive expanse (which is between the balloons) so as properly to engage the heart wall. Thereafter, the needle may be withdrawn.

Then, with the use of a conventional electrical heart-pacing source, one output terminal of this source may be connected to supply pulses to the expanse on the tube, and the other output terminal connected to another electrode which is suitably attached to the outside of a person's body. Further, the central axial passage through the tube may be used for the immediate injection of desired medications into the heart cavity.

Various other objects and advantages which are attained by the invention will become more fully apparent as the description which now follows is read in conjunction with the accompanying drawings.

DESCRIPTION OF THE DRAWINGS

FIG. 1 is a fragmentary side elevation of an instrument constructed in accordance with the present invention, with this instrument shown in the position which it might occupy just following transthoracic insertion through a person's chest and heart walls.

FIG. 2 is an enlarged cross-sectional view taken generally along the line 2—2 in FIG. 1.

FIGS. 3 and 4 are views on about the same scale as FIG. 1 illustrating post-insertion steps resulting in proper final placement of the distal end of the instrument of FIG. 1 with respect to a heart wall.

DETAILED DESCRIPTION OF THE INVENTION

Turning now to the drawings, and referring first to FIGS. 1 and 2, indicated generally at 10 is a cardiac resuscitation instrument as contemplated by the present invention. Instrument 10 includes an elongated flexible tube 12 which is intended to be used in conjunction with an elongated rigid needle, such as the conventional catheter needle shown at 14. In FIG. 1, needle 14 is shown fully inserted in the central axial passage 12a of the tube, with the beveled and sharpened distal end 14a of the needle projecting outwardly and beyond the right end of tube 12 in FIG. 1, because of the needle's greater length.

Considering materials which are or may be used in the body of tube 12, and of needle 14, as was mentioned above, the tube is flexible, and preferably is made of a suitable flexible plastic material, such as a flexible polyethylene. As will become apparent, flexibility in tube 12 is a desirable feature in minimizing stressing and damage of the heart and chest tissue adjacent it, as well as in minimizing patient discomfort, under circumstances with its being left indwelling in a person's chest after successful cardiac resuscitation. Needle 14, on the other hand, is preferably quite rigid, and may be made of a suitable stainless steel.

Needle 14 herein has an overall length of about 8 inches, with the long slender prong in the needle being of about 16-gauge size. The overall length of tube 12 is about 6 inches.

As can be seen clearly in FIG. 1, the body of tube 12 includes an elongated slender central portion 12b which merges, at the distal end of the tube, with a tapered nose portion 12c, and at the proximal end of the tube with an enlarged coupling portion 12d.

Provided within the wall of the tube are three elongated passages which extend substantially parallel with central passage 12a. These passages are shown at 16, 18, 20. The particular lengths and functions of these three passages will be discussed shortly.

Referring again particularly to FIG. 1, mounted on the outside of portion 12b of the tube, adjacent the distal end thereof, are a pair of conventional, normally deflated, inflatable balloons 22, 24. These balloons completely surround the outside of tube portion 12b, and are spaced apart axially along this portion by a distance which is about the same as the expected thickness of the wall in a person's heart. This distance might typically be about 4-mm. The right end in FIG. 1 of previously mentioned passage 16 terminates adjacent balloon 22, and is angled beneath this balloon so as to communicate with the latter for the purpose of enabling selective and independent inflation and deflation of the balloon. Similarly, the right end of passage 18 communicates with balloon 24. In FIG. 1, balloons 22, 24 are shown completely deflated in solid outline, with balloon 24 being shown fully inflated in dash-dot outline.

Provided on the outside of tube portion 12b, in the space between the two balloons, and substantially completely surrounding the tube portion, is an electrically conductive expanse, or band, 26. Previously mentioned passage 20 terminates adjacent band 26, and contains an elongated conductor 28 (see FIG. 2) which connects with the band.

Provided for inflating and deflating the balloons are two conventional squeeze bulbs 30, 32 which are coupled through flexible hoses 34, 36, respectively, and through coupling portion 12d in the tube, with the proximal or left ends of passages 16, 18, respectively. Conductor 28, adjacent the left end of passage 20 in FIG. 1 connects with an external conductor 38 which is provided with an end connector shown at 40.

Explaining now how the instrument of the invention may be used, when it is decided to perform transthoracic cardiac resuscitation, needle 14 is fully inserted through tube 12 as shown in FIG. 1. Initially, balloons 22, 24 are fully deflated, and connector 40 may be left unconnected to anything external to the instrument. With the sharpened end of the needle thus exposed, and with the needle rigidifying tube 12, the assembly of the needle and tube is thrust through a person's chest wall so as to drive the distal end of tube 12 through the myocardial wall of a person's heart, and into the heart's right ventricle, for example. In FIGS. 1, 3 and 4, a person's chest wall and heart wall are shown in greatly simplified forms, and are designated CW and HW, respectively.

Preferably, and as is contemplated herein, the tube is thrust sufficiently far so as to place balloon 24 initially inwardly of and out of contact with the heart wall. This situaion is shown in FIG. 1. Such an initial placement of the distal end of the tube is an important step in assuring proper final placement of the tube for resuscitation use. With the tube in this initial condition of penetration, balloon 24 alone is inflated to its fully inflated condition, which is shown in dashed outline in FIG. 1, and in solid outline in FIGS. 3 and 4.

With inflation of balloon 24, removal of the tube is prevented, and further, proper final positioning of the tube in the heart wall is assured. More specifically, what next follows is that the assembly of the needle and tube is slightly retracted so as to place balloon 24 against the inside face of the heart wall, as shown in FIG. 3. As will be evident from a study of FIG. 3, such retraction results in band 26 being placed directly within the heart wall, and with balloon 22 being placed on the outside of the heart wall.

Thereafter, balloon 22 is fully inflated to the condition shown for it in solid outline in FIG. 4, whereupon it rests against the outside of the heart wall. Needle 14 is then withdrawn whereupon tube 12 is derigidified.

The instrument is now in a condition for resuscitation use. It will be apparent that central passage 12a in the tube provides direct immediate access to the heart ventricular cavity for the injection of desired medications. Electrical pacing pulses may be supplied to band 26, with another suitable pacing electrode attached in a conventional manner to the outside of a person's body. Balloons 22, 24, which clamp against opposite sides of the heart wall, prevent "working" of the tube in the wall of the heart, and in the chest, and hence prevent both heart wall damage, and inadvertent displacement of the tube.

It will thus be apparent that a convenient one-shot transthoracic insertion is possible with the present instrument, with subsequent readily obtained correct final placement of the tube's distal end. With a catheter needle, or the like, used as a temporary rigidifier and carrier for the tube, the tube is made sufficiently stiff for transthoracic insertion, yet can later be derigidifed to minimize patient discomfort and tissue damage. Because the needle fits within the tube, the outside of the tube defines the final sizes of the punctures made during insertion, and hence forms a tight fit in these punctures minimizing bleeding around a puncture site while the tube remains indwelling.

With final placement of the tube, the tube's exposed distal end is properly positioned for injection of medications, and the electrical pacing band is properly located within a heart wall.

When it is desired to remove the instrument, this may be done simply by fully deflating the balloons, and then retracting the tube.

While a preferred embodiment of the invention has been described herein, it is appreciated that variations and modifications are possible and may be made without departing from the spirit of the invention.

It is claimed and desired to secure by letters patent:

1. A transthoracic, cannula-type cardiac resuscitation instrument comprising
   an elongated catheter needle, or the like, of a certain length,
   an elongated flexible tube having distal and proximal ends, and including, extending along its length which is less than said certain length, wall means defining an elongated double-open-ended passage for accommodating the slidable and removable reception therein of said needle, with said needle when received therein being circumferentially surrounded by said tube with an end of said needle projecting axially from said distal end of the tube,
   means mounted on the outside of said tube defining an exposed electrically conductive expanse adjacent but inwardly of the tube's distal end,
   conductor means connected to said expanse for operatively connecting said expanse to electrical pacing apparatus,
   a pair of spaced, selectively and independently changeable-geometry elements mounted on the outside of said tube on axially opposite sides of said expanse, and
   means operable for selectively altering the geometry of each element by changing each element's overall radial projection from the outside of said tube.

2. The instrument of claim 1, wherein said conductive expanse takes the form of a band extending about said tube.

3. The instrument of claim 1, wherein each of said elements extends circumferentially about said tube, and a change in the geometry of an element affects its radial projection at all points about the outside of the tube.

4. The instrument of claim 1, wherein each of said elements comprises an inflatable balloon-like device, and said tube is provided with a passage means for each of said devices, communicating with the same and accommodating the selective inflation and deflation of the device.

5. A transthoracic, cannula-type cardiac resuscitation instrument comprising
   an elongated catheter needle, or the like, of a certain length, an elongated flexible tube having distal and proximal ends, and including, extending along its length which is less than said certain length, wall means defining an elongated double-open-ended passage for accommodating the slidable and removable reception therein of said needle, with said needle when received therein being circumferentially surrounded by said tube with an end of said needle projecting axially from said distal end of the tube, means mounted on the outside of said tube defining an exposed electrically conductive expanse adjacent but inwardly of the tube's distal end, conductor means connected to said expanse for operatively connecting said expanse to electrical pacing apparatus, a pair of spaced, normally deflated inflatable-deflatable elements mounted on and circumferentially surrounding the outside of said tube on axially opposite sides of said conductive expanse, and means for selectively inflating and deflating said elements.

6. The instrument of claim 5, wherein said conductive expanse takes the form of a band extending about said tube.

7. The instrument of claim 5, wherein, said means for selectively inflating and deflating each element includes a passage extending through said tube and communicating with each element.

8. A transthoracic, cannula-type cardiac resuscitation instrument comprising an elongated catheter needle, or the like, of a certain length, an elongated flexible tube having distal and proximate ends, and including extending along its length, which is less than said certain length, cylindrical wall means defining an axially central, double-open-ended passage for accommodating the slidable reception therein of said catheter needle or the like with an end of said needle projecting axially from one end of said tube, a pair of normally deflated fluid-inflatable means secured adjacent and surrounding said one end of said tube, said fluid-inflatable means being spaced longitudinallly on said end, and separated by a distance substantially equaling the thickness expected in the myocardial wall of a person's heart, elongated fluid passage means extending along said tube within said wall means and communicating with said fluid-inflatable means for accommodating the selective and independent inflation and deflation of each of said fluid-inflatable means, means defining an electrically conductive expanse exposed on the outside of said tube in the region between said fluid-inflatable means, and elongated electrical conductor means connected to said expanse and extending along said tube within said wall means.

9. The instrument of claim 8, wherein said conductive expanse takes the form of a band extending about said tube.

10. The instrument of claim 8, wherein each of said fluid-inflatable means extends circumferentially about said tube.

11. Transthoracic, cannula-type cardiac resuscitation apparatus comprising an elongated catheter needle or the like having a sharpened end, an elongated flexible tube including distal and proximal ends, and containing, extending along its length, wall means defining a double-open-ended passage for accommodating the slidable and removable reception of said needle, said tube having a length which is less than that of said needle, whereby when said needle is received therein its sharpened end projects from said distal end of the tube, means disposed on the outside of said tube defining an exposed electrically conductive expanse adjacent but inwardly of the tube's distal end, conductor means for operatively connecting said expanse to electrical pacing apparatus, a pair of spaced, normally deflated inflatable-deflatable elements mounted on and circumferentially surrounding the outside of said tube on axially opposite sides of said conductive expanse, and means for selectively inflating and deflating said elements.

12. The apparatus of claim 11, wherein said conductive expanse takes the form of a band extending about said tube.

13. The apparatus of claim 11, wherein said means for selectively inflating and deflating each element includes a passage means extending through said tube and communicating with each element.

* * * * *